United States Patent [19]

Cardon

[11] 4,120,952

[45] * Oct. 17, 1978

[54] METHOD FOR THE TREATMENT OF DIARRHEA IN MONOGASTRIC ANIMALS

[75] Inventor: Bartley P. Cardon, Tucson, Ariz.

[73] Assignee: Arizona Feeds, Tucson, Ariz.

[ * ] Notice: The portion of the term of this patent subsequent to Oct. 7, 1992, has been disclaimed.

[21] Appl. No.: 771,176

[22] Filed: Feb. 22, 1977

Related U.S. Application Data

[63] Continuation-in-part of Ser. No. 619,903, Oct. 6, 1975, Pat. No. 4,010,262.

[51] Int. Cl.² .......................................... A61K 31/715
[52] U.S. Cl. .................................................. 424/180
[58] Field of Search ......................................... 424/180

[56] References Cited

U.S. PATENT DOCUMENTS

| 3,911,114 | 10/1975 | Cardon | 424/180 |
| 4,010,262 | 4/1977 | Cardon et al. | 424/180 |

*Primary Examiner*—Sam Rosen
*Attorney, Agent, or Firm*—Wills, Green & Meuth Law Corporation

[57] ABSTRACT

Monogastric animals such as pigs, humans and equines are given an oral dosage of pregelatinized starch in paste form or in a liquid mixture upon the occurrance of diarrhea.

10 Claims, No Drawings

METHOD FOR THE TREATMENT OF DIARRHEA IN MONOGASTRIC ANIMALS

CROSS-REFERENCE TO RELATED APPLICATION

This application is a continuation-in-part of application Ser. No. 619,903, filed Oct. 6, 1975, now U.S. Pat. No. 4,010,262.

BACKGROUND AND SUMMARY OF THE INVENTION

Newborn pigs usually remain with the sow for approximately 20 to 30 days, at which time each weighs approximately 15 pounds. The pigs are then taken from the sow, placed in community pens and fed a dry feed. This weaning of the pigs and placing them in community pens causes as many as 50% of the pigs to have scours or diarrhea within two to three days after being placed in the pens.

Of the 50% which develop scours, it is not unusual for one-fifth or 20% of the pigs with diarrhea to die, without treatment. Approximately 20% of the pigs with scours will recover without an appreciable loss of weight, but the other 60% of scoured pigs will lose a significant amount of weight through rapid dehydration, and this loss of weight must be made up through additional time and additional feed. Obviously, there is a tremendous economic loss occasioned by the death of approximately ten percent of all weaned pigs, and a significant weight loss suffered by 30% of all weaned pigs.

Another monogastric which is highly susceptible to scours or diarrhea is homo sapien . . . as a newborn infant, during various states of development and after maturity. Newborn infants are highly susceptible to diarrhea and adults are often troubled with diarrhea as a result of traveling to countries foreign to the United States, where the drinking water might not be as clean as that to which they have been accustomed.

Yet another monogastric which is troubled with scours or diarrhea, is the equine.

Accordingly, it is an object of the present invention to provide a novel method for treating scours or diarrhea in monogastric animals, which is relatively quick-acting and which does not have any harmful side effects.

A further object is to provide such a method in which the material can be administered orally in the form of a paste or a liquid mixture.

Another object is to provide such a method which is especially safe and effective for the treatment of humans during all stages of development and at maturity. More particularly, it is an object to provide such a method which is especially suitable for the treatment of newborn infants.

Yet another object is to provide a novel method for treating other monogastrics such as pigs and horses, whereby they can be quickly returned to normal without any appreciable weight loss or harmful side effects.

A further object of the present invention is to provide such a method which is relatively inexpensive and easy to use.

We have discovered that the aforementioned objects and advantages are achieved by feeding to monogastric animals, an effective amount of pregelatinized starch in a paste form or in a liquid mixture.

DETAILED DESCRIPTION

As mentioned above, pigs are weaned when they are about one month of age, at which time they are placed in community pens and fed a dry feed mix. At the present time, 50% of the young pigs will develop scours within two or three days. Of the scoured pigs, some will recover without treatment and without an appreciable weight loss, whereas a significant number will die and an even greater number will lose a significant amount of weight before recovering.

We have discovered that the incidence of scours in such newly weaned pigs can be greatly reduced, and in many instances practically eliminated, by feeding to the animal a daily ration of pregelatinized starch in an amount of approximately 5 grams, and preferably in a paste form.

The pregelatinized starch which we have used with considerable success was obtained from The Hubinger Company, Keokuk, Iowa, and sold by it under the designation "OK PRE-GEL". This is a pure, highly refined corn starch which is pregelatinized in water, dehydrated and pulverized to a white, finely granulated solid having a uniform particle size and a moisture content of about 3.5 to about 8.0%. The water absorbtion capacity of this pregelatinized starch is greater than 15 to 1.

We have successfully administered the pregelatinized strach to newly weaned pigs by mixing it with enough water to form a viscous paste, inserting a soft piece of rubber tubing past the trachea and into the esophagus of the animal, and then forcing the appropriate amount of pregelatinized starch paste through the tube. Tests were made to determine the effectiveness of the pregelatinized starch paste in reducing the incidence of scours in weaned pigs, and the treatment of scoured pigs using the same composition and method.

EXAMPLE NO. 1

A group of newly weaned feeder pigs, approximately 20 days of age and weighing between about 13 and 15 pounds each, were placed in steel cages and fed a 16% protein non-medicated pellet on a free choice basis. Water was also available on a free choice basis.

On the first day, each pig was assigned to one of the following groups:
(a) control: no pregelatinized starch,
(b) 1.0 grams of pregelatinized starch per day, and
(c) 5.0 grams of pregelatinized starch per day.

All pigs were observed for incidence of diarrhea, and scoured pigs were immediately removed from the trial. Set forth below are the tabulated results:

|  | Grams of Pregelatinized Starch, Per Day | | |
| --- | --- | --- | --- |
|  | 0 | 1.0 | 5.0 |
| Number of pigs | 5 | 5 | 5 |
| Number with diarrhea | 5 | 2 | 0 |
| Time to onset of diarrhea, hours[1] | 36.0 | 48.0 | — |

From the time pigs were placed in cages until diarrhea was observed.

As shown by the tabulated results, all control pigs were observed to have diarrhea after 36 hours on trial. Forty percent of the pigs given 1 gram of pregelatinized starch per day, scoured after 48 hours on trial, and 5 grams of pregelatinized starch per day completely prevented any scouring.

EXAMPLE NO. 2

A further trial was conducted to determine the efficacy of the pregelatinized starch to control and stop the diarrhea.

For this purpose, 20 newly weaned feeder pigs were separated out as soon as scouring was detected.

Eight of the pigs were classified as control, and remained on normal free choice food and water, without any special medication.

The remaining 12 pigs were each fed 5 grams of pregelatinized starch in paste form, once a day. The 12 treated pigs fully recovered with an average treatment of 2 days or 48 hours.

After the eight control pigs remained untreated for 48 hours, each was fed 5 grams per day of pregelatinized starch in paste form, until fully recovered. The control pigs which did not receive the pregelatinized starch until after scouring for 48 hours, required an average of 3 days or 3 dosages before they fully recovered.

Thus, it has been clearly established that pregelatinized starch, fed to newly weaned pigs at a rate of about 5 grams per day, will drastically reduce the incidence of scours, and if scours occur, will cause the diarrhea to stop within a matter of a few days, and before there is any appreciable weight loss.

Equally successful results have been achieved in orally administering to humans, approximately 30 grams of pregelatinized starch in a liquid mixture of water, orange juice or milk. A few of these are set forth below.

EXAMPLE NO. 3

Subject:
44 year old caucasian female of generally good health, residing at Tucson, Arizona.

Background:
In July 1976, subject became aware of stomach cramps which worsened throughout the day. A stool of fluid consistency was passed during the evening and persisted until the following morning.

Treatment:
Two tablespoons (approximately 30 grams) of pregelatinized starch was mixed with 8 ounces of cold milk. The mixture was flavored with chocolate and taken orally at noon.

Results:
The cramps diminished within 3 hours of ingesting the treatment mixture. A gelatinous stool was passed in the evening. Stool formations returned to normal the following day and continued to be normal.

EXAMPLE NO. 4

Subject:
45 year old male caucasion of generally good health, residing at Tucson, Arizona.

Background:
While on a trip to Santiago, Chile, in October, 1976, subject ate a dinner of local seafood. Early the next morning, the subject suffered profuse fluid diarrhea. Upon returning to Tucson the following day, the subject continued to have diarrhea of the same nature for six days without other signs of discomfort.

Treatment:
On the morning of the sixth day, treatment was initiated with pregelatinized starch. 2 rounded tablespoons (approximately 30 grams) of pregelatinized starch were mixed in milk (flavored with chocolate) and consumed quickly. Treatment was repeated that evening and again the following morning.

Results:
One fluid stool was observed within 2 hours after the initial treatment. That evening, a gelatinous stool was passed and by noon of the following day stool formation had returned to normal and remained so.

EXAMPLE NO. 5

Subject:
45 year old male caucasian of generally good health, residing at Tucson, Ariz.

Background:
In 1976, on the morning after returning from a trip to Guadalajara, Mexico, the subject suffered from intestinal discomfort and passed a fluid stool at about 12:00 Noon.

Treatment:
One dose consisting of 2 rounded tablespoons (approximately 30 grams) of pregelatinized starch were mixed in 8 ounces of chocolate flavored milk and was taken orally at about 12:30 P.M.

Results:
The intestinal discomfort subsided slowly and was not evident by 4:00 P.M. on the same day. The subject passed no stool until the afternoon of the following day, at which time the stool was normal. Normal stools were passed on successive days without recurrence of the diarrhea.

EXAMPLE NO. 6

Subject:
35 year old caucasian male of generally excellent health and no history of chronic digestive disorders.

Background:
In November 1974, the subject returned from Hermosillo, Sonora, Mexico, after a one-day consulting trip. During the first evening home, the subject became stricken with lower abdominal cramps followed in 2 hours by a perfuse, watery diarrhea. These symptoms continued unabated until 12:00 midnight.

Treatment:
2 tablespoons (approximately 30 grams) of pregelatinized starch were mixed into 8 ounces of cold water and consumed quickly. Treatment was not repeated.

Results:
The cramps diminished in 2 hours after ingesting the pregelatinized starch mixture. There was no stool formation until 8:00 that evening (20 hours post-treatment) at which time a normal stool was passed. Subject reported normal stool formation from then on.

EXAMPLE NO. 7

Subject:
23 year old caucasion female of generally good health, residing at Tucson, Ariz.

Background:

On November 1, 1976, subject had an upset stomach accompanied by diarrhea. Stool formation was extremely watery.

Treatment:

At 9:00 A.M. on November 1, 2 tablespoons (approximately 30 grams) of pregelatinized starch were mixed into 8 ounces of chocolate milk and consumed immediately. Treatment was not repeated.

Results:

Stomach cramps ceased 1 hour after treatment with the pregelatinized starch. The subject did not pass a stool for 5 hours post-treatment, at which time a gelatinous stool was passed. A second stool was passed during the evening which was normal. All stools thereafter were normal.

EXAMPLE NO. 8

Subject:

28 year old caucasian female of generally good health, residing at Tucson, Ariz.

Background:

On June 15, 1976, subject felt a precipitous onset of stomach cramps, nausea, and diarrhea. Diarrhea was extremely watery and fetid; occurring once each 30 minutes.

Treatment:

3 tablespoons (approximately 45 grams) of pregelatinized starch were mixed into 1 ounce of cocoa-mix and 6 ounces of water. Mixture was consumed orally at 11:00 A.M. on June 15. Treatment was not repeated.

Results:

Subject felt uneasy for another hour, after which the stomach cramps stopped completely. There was no stool passed for 3 days after treatment, at which time normal stool formation was noticed. Although the time from treatment to first stool formation was unique, the subject has a normal stool cycle of two days.

EXAMPLE NO. 9

Subject:

34 year old caucasian female of generally good health, residing at Tucson, Ariz.

Background:

On January 19, 1977, subject returned from evening bowling party and felt nauseous. Complained of stomach cramps and began passing watery stools. By the next evening (January 20), cramps and diarrhea were still present.

Treatment:

Subject mixed 2 tablespoons (approximately 30 grams) pregelatinized starch with 8 ounces of orange juice and consumed this mixture at 9:30 P.M. January 20.

Results:

By 10:00 P.M. (12 hours post treatment), the stomach cramps had abated and by 8:00 the following morning the subject passed a normal stool.

EXAMPLE NO. 10

Subject:

4 members of the same family (49 years old caucasian male, 49 year old caucasian female 19 year old caucasian female, 20 year old caucasian male) all of generally good health and residing at Chicago, Ill.

Background:

On December 24, 1976, all four family members complained of flu symptoms immediately after dinner. Temperatures ranged from 100° to 101.5° F. Each subject had water diarrhea and stomach cramps. Diarrhea was watery and fetid.

Treatment:

The 2 male subjects each consumed a mixture of 2 tablespoons (approximately 30 grams) of pregelatinized starch mixed in orange juice at 9:30 P.M. Treatment was not repeated. The female subjects did not treat for the symptoms.

Results:

The male subjects noted that the stomach cramps abated within 2 hours of stach ingesting. By morning the male subjects were both passing normal stools. Both female subjects continued to have cramps and diarrhea for $2\frac{1}{2}$ days.

Excellent results have also been obtained in the treatment of equines, using pregelatinized starch.

EXAMPLE NO. 11

Subject:

3 year old gelding with no history of chronic diarrhea.

Background:

Owner called veterinarian and mentioned that horse was diarrheic. On observation, veterinarian diagnosed sand colic.

Treatment:

Approximately 60 grams of pregelatinized starch were mixed in approximately 2 quarts of water and given the horse orally. Treatment was not repeated.

Results:

The diarrhea cleared up within 1 day following treatment. Veterinarian reported sand was being passed in feces.

EXAMPLE NO. 12

Subject:

Young stallion, brought to Tucson from the Southeast.

Background:

Owner called veterinarian and stated that horse was extremely diarrheic and had been that way for 6-8 hours. Temperature was slightly abnormal on the low side. Animal hyper-active.

Treatment:

Approximately 30 grams of pregelatinized starch were mixed with 18 ounces of cold water and administered orally with a standard dose syringe at 8:00 p.m.

Results:

By morning, the horse passed a formed stool with a gelatinous sheen. A second, similar dosage was administered that morning. Normal stools were observed by evening. Owner stated that the material was extremely palatable to the animal, and, unlike most drench materials, did not cause excessive salivation.

From these test results, it is believed clear that the use of pregelatinized starch in a liquid mixture, ingested orally by monogastrics upon the occurrence of diarrhea, is extremely effective in stopping the diarrhea within a relatively short period of time.

I claim:

1. The method of treating monogastric animals suffering from diarrhea, comprising orally administering to the animal an effective amount of pregelatinized starch in a liquid mixture.

2. The method according to claim 1, in which the animal is from the group consisting of swine, equines and humans.

3. The method according to claim 1, in which the animal is a horse and the amount of pregelatinized starch is approximately thirty grams.

4. The method according to claim 3, in which the pregelatinized starch is mixed with water prior to administering it to the horse.

5. The method according to claim 1, in which the animal is an adult human and the amount of pregelatinized starch is approximately thirty grams.

6. The method according to claim 5, in which the pregelatinized starch is mixed with water prior to administering it to the human.

7. The method according to claim 5, in which the pregelatinized starch is mixed with milk prior to administering it to the human.

8. The method according to claim 4, in which the ratio of pregelatinized starch to water, is approximately one to eight, by weight.

9. The method according to claim 6, in which the ratio of pregelatinized starch to water is approximately one to eight, by weight.

10. The method according to claim 7, in which the ratio of pregelatinized starch to milk is approximately one to eight, by weight.

* * * * *